United States Patent
Murdock

(10) Patent No.: US 6,374,136 B1
(45) Date of Patent: Apr. 16, 2002

(54) ANHYDROUS DRUG RESERVOIR FOR ELECTROLYTIC TRANSDERMAL DELIVERY DEVICE

(75) Inventor: Thomas O. Murdock, Vadnais Height, MN (US)

(73) Assignee: Alza Corporation, Mountain View, CA (US)

(*) Notice: Subject to any disclaimer, the term of this patent is extended or adjusted under 35 U.S.C. 154(b) by 0 days.

(21) Appl. No.: 09/208,808

(22) Filed: Dec. 9, 1998

Related U.S. Application Data

(60) Provisional application No. 60/071,256, filed on Dec. 22, 1997.

(51) Int. Cl.⁷ .................................................. A61N 1/30
(52) U.S. Cl. ............................ 604/20; 514/772; 424/449
(58) Field of Search ..................... 604/20, 289, 890.1, 604/304, 305, 307; 424/449, 448, 447; 602/48; 514/772

(56) References Cited

U.S. PATENT DOCUMENTS

| | | | |
|---|---|---|---|
| 3,991,755 A | 11/1976 | Vernon et al. ............ 128/172.1 |
| 4,141,359 A | 2/1979 | Jacobsen et al. ......... 128/172.1 |
| 4,250,878 A | 2/1981 | Jacobsen et al. ....... 128/207.21 |
| 4,383,529 A | 5/1983 | Webster ....................... 604/20 |
| 4,398,545 A | 8/1983 | Wilson ........................ 128/798 |
| 4,474,570 A | 10/1984 | Ariura et al. ................. 604/20 |
| 4,731,049 A | 3/1988 | Parsi .............................. 604/20 |
| 4,764,164 A | 8/1988 | Sasaki ........................... 604/20 |
| 4,842,577 A | 6/1989 | Konno et al. ................. 604/20 |
| 4,878,893 A | 11/1989 | Sibalis et al. ................. 604/20 |
| 4,927,408 A | * 5/1990 | Haak et al. .................... 604/20 |
| 4,940,456 A | 7/1990 | Sibalis et al. ................. 604/20 |
| 5,080,646 A | * 1/1992 | Theeuwes et al. ............. 604/20 |
| 5,158,537 A | 10/1992 | Haak et al. .................... 604/20 |
| 5,310,404 A | * 5/1994 | Gyory et al. .................. 604/20 |
| 5,385,543 A | 1/1995 | Haak et al. .................... 604/20 |
| 5,464,387 A | * 11/1995 | Haak et al. .................... 604/20 |
| 5,496,266 A | * 3/1996 | Haak et al. .................... 604/20 |
| 5,503,632 A | * 4/1996 | Haak ............................. 604/20 |
| 5,533,971 A | * 7/1996 | Phipps .......................... 604/20 |
| 5,573,668 A | * 11/1996 | Grosh et al. ................ 210/490 |
| 5,624,415 A | * 4/1997 | Cormier et al. ............. 604/290 |
| 5,645,527 A | 7/1997 | Beck ............................. 604/20 |
| 5,647,844 A | * 7/1997 | Haak et al. .................... 604/20 |
| 5,668,170 A | * 9/1997 | Gyory ......................... 514/449 |
| 5,730,716 A | * 3/1998 | Beck et al. .................... 604/20 |
| 5,736,580 A | * 4/1998 | Huntington et al. ........ 514/772 |
| 5,908,400 A | * 6/1999 | Higo et al. .................... 604/20 |
| 5,993,435 A | * 11/1999 | Haak et al. .................. 604/501 |
| 6,057,374 A | * 5/2000 | Huntington et al. ........ 514/772 |

FOREIGN PATENT DOCUMENTS

| | | | |
|---|---|---|---|
| GB | 410009 | 10/1933 | |
| WO | WO 93/18727 | 9/1993 | ........... A61F/13/00 |
| WO | WO 93/24177 | 12/1993 | ........... A61N/1/30 |
| WO | WO 96/05884 | 2/1996 | ........... A61N/47/10 |

* cited by examiner

*Primary Examiner*—Richard K. Seidel
*Assistant Examiner*—Cris Rodriguez
(74) *Attorney, Agent, or Firm*—D. Byron Miller; Owen J. Bates

(57) ABSTRACT

An electrode assembly and a method of forming an anhydrous reservoir layer of an electrode assembly in an electrotransport transdermal agent delivery device are provided. The reservoir layer is adapted to be placed in agent-transmitting relation with a body surface and an electrode in electrical contact with a power source and the reservoir layer. The method includes the steps of dissolving a beneficial agent in a solvent, applying the solvent and dissolved beneficial agent to a surface of a hydrophilic polymer filtration membrane, removing the solvent from the surface of the filtration membrane, and disposing the beneficial agent/filtration membrane within the electrode assembly.

16 Claims, 3 Drawing Sheets

ANHYDROUS DRUG RESERVOIR FOR ELECTROLYTIC TRANSDERMAL DELIVERY DEVICE

RELATED APPLICATIONS

This application claims the benefit of U.S. Provisional Application No. 60/071,256, filed on Dec. 22, 1997.

TECHNICAL FIELD

The present invention is directed to a device for delivering an agent transdermally or transmucosally by electrolytic transdermal delivery, and more particularly, to an anhydrous drug reservoir of an electrolytic transdermal delivery device having which can be hydrated just before applying the device to the body, and to a method of producing the same.

BACKGROUND OF THE INVENTION

Iontophoresis, according to Dorland's Illustrated Medical Dictionary, is defined to be "the introduction, by means of electric current, of ions of soluble salts into the tissues of the body for therapeutic purposes." Iontophoretic devices have been known since the early 1900's. British patent specification No. 410,009 (1934) describes an iontophoretic device which overcame one of the disadvantages of such early devices known to the art at that time, namely the requirement of a special low tension (low voltage) source of current which meant that the patient needed to be immobilized near such source. The device of that British specification was made by forming a galvanic cell from the electrodes and the material containing the medicament or drug to be delivered transdermally. The galvanic cell produced the current necessary for iontophoretically delivering the medicament. This ambulatory device thus permitted iontophoretic drug delivery with substantially less interference with the patient's daily activities.

More recently a number of United States patents have issued in the electrolytic transdermal delivery field, indicating a renewed interest in this mode of drug delivery. For example, U.S. Pat. No. 3,991,755 issued to Vernon et al., U.S. Pat. No. 4,141,359 issued to Jacobsen et al., U.S. Pat. No. 4,398,545 issued to Wilson, and U.S. Pat. No. 4,250,878 issued to Jacobsen disclose examples of iontophoretic devices and some applications thereof. The iontophoresis process has been found to be useful in the transdermal administration of medicaments or drugs including lidocaine hydrochloride, hydrocortisone, fluoride, penicillin, dexamethasone sodium phosphate, insulin and many other drugs. Perhaps the most common use of iontophoresis is in diagnosing cystic fibrosis by delivering pilocarpine salts iontophoretically. The pilocarpine stimulates sweat production; the sweat is then collected and analyzed for its chloride content to detect the presence of the disease.

In presently known iontophoretic devices, at least two electrodes are used. Both of these electrodes are disposed so as to be in intimate electrical contact with some portion of the skin of the body. One electrode, called the active or donor electrode, is the electrode from which the ionic substance, medicament, drug precursor or drug is delivered into the body by iontophoresis. The other electrode, called the counter or return electrode, serves to close the electrical circuit through the body. In conjunction with the patient's skin contacted by the electrodes, the circuit is completed by connection of the electrodes to a source of electrical energy, e.g., a battery. For example, if the ionic substance to be delivered into the body is positively charged (i.e., a cation), then the anode will be the active electrode and the cathode will serve to complete the circuit. If the ionic substance to be delivered is negatively charged (i.e. an anion), then the cathode will be the active electrode and the anode will be the counter electrode.

Alternatively, both the anode and cathode may be used to deliver drugs of opposite charge into the body. In such a case, both electrodes are considered to be active or donor electrodes. For example, the anode can deliver a positively charged ionic substance into the body while the cathode can deliver a negatively charged ionic substance into the body.

It is also known that iontophoretic delivery devices can be used to deliver an uncharged drug or agent into the body. This is accomplished by a process called electroosmosis. Transdermal delivery of neutral compounds by the phenomenon of electroosmosis is described by Hermann Rein in Zeitschrift fur Biologie, Bd. 8 1, pp 125–140 (1924) and the transdermal delivery of non-ionic polypeptides by the phenomenon of electroosmosis is described in Sibalis et al., U.S. Pat. Nos. 4,878,892 and 4,940,456. Electroosmosis is the transdermal flux of a liquid solvent (e.g., the liquid solvent containing the uncharged drug or agent) which is induced by the presence of an electric field imposed across the skin by the donor electrode. Similarly, electrophoresis is the transdermal flux of both the solute and the liquid solvent in an electric field. As used herein, the terms "electrotransport" and "electrolytic transdermal delivery" encompass both the delivery of charged ions as well as the delivery of uncharged molecules by the associated phenomenons of iontophoresis, electroosmosis, and electrophoresis.

Electrotransport delivery devices generally require a reservoir or source of the beneficial agent (which is preferably an ionized or ionizable agent or a precursor of such agent) to be iontophoretically delivered or introduced into the body. Examples of such reservoirs or sources of ionized or ionizable agents include a pouch or cavity as described in the previously mentioned Jacobsen, U.S. Pat. No. 4,250,878, a porous sponge or pad as disclosed in Jacobsen et al., U.S. Pat. No. 4,141,359, or a preformed gel body as described in Webster, U.S. Pat. No. 4,383,529, and Ariura et al., U.S. Pat. No. 4,474,570. Such drug reservoirs are electrically connected to the anode or the cathode of an electrotransport device to provide a fixed or renewable source of one or more desired agents.

Electrotransport delivery devices which are attachable at a skin surface and rely on electrolyte fluids to establish electrical contact with such skin surfaces can be divided into at least two categories. The first category includes those devices which are prepackaged with the liquid electrolyte contained in the electrode receptacle. The second type of device uses drystate electrodes whose receptacles or reservoirs are customarily filled with liquid drug/electrolyte immediately prior to application to the body. With both types of devices, the user currently experiences numerous problems which make their use both inconvenient and problematic.

With respect to the prefilled device, storage is a major concern. Many drugs have poor stability when in solution. Accordingly, the shelf life of prefilled iontophoretic drug delivery devices is unacceptably short. Corrosion of the electrodes and other electrical components is also a potential problem with prefilled devices. For example, the return electrode assembly will usually contain an electrolyte salt such as sodium chloride which over time can cause corrosion of metallic and other electrically conductive materials in the electrode assembly. Leakage is another serious problem with prefilled iontophoretic drug delivery devices. Leakage of drug or electrolyte from the electrode receptacle can result in an inoperative or defective state. Furthermore, such prefilled devices are difficult to apply because the protective seal which covers the electrode opening and retains the fluid within the receptacle cavity must be removed prior to application on the skin. After removal of this protective seal, spillage often occurs in attempting to place the electrode on the skin. Such spillage impairs the desired adhesive contact of the electrode to the skin and also voids a portion of the receptacle cavity. The consequent loss of drug or electrolyte fluid tends to disrupt electrical contact with the electrode plate contained therein and otherwise disrupts the preferred uniform potential gradient to be applied.

Although dry-state electrodes have numerous advantages in ease of storage, several problems remain. For example, the drug and electrolyte receptacles of such a device are conventionally filled through an opening prior to application of the device to the patient's skin. Therefore, the same problem of spillage and loss of drug or electrolyte upon application occurs as with the pre-filled electrode.

Frequently, such electrodes are not well structured to develop the proper uniform current flow required in iontophoresis applications. Such nonuniform current flow may result from the occurrence of air pockets within the receptacle cavity at the skin surface. Such effects are particularly troublesome in electrolytic transdermal delivery applications, where a nonuniform current distribution may result in excessive skin irritation or "burning".

More recently, electrotransport delivery devices have been developed in which the donor and counter electrode assemblies have a "multilaminate" construction. In these devices, the donor and counter electrode assemblies are each formed of multiple layers of (usually) polymeric matrices. For example, Parsi, U.S. Pat. No. 4,731,049, discloses a donor electrode assembly having hydrophilic polymer based electrolyte reservoir and drug reservoir layers, a skin-contacting hydrogel layer, and optionally, one or more semipermeable membrane layers. In addition, Ariura et al., U.S. Pat. No. 4,474,570, discloses a device wherein the electrode assemblies include a conductive resin film electrode layer, a hydrophilic gel reservoir layer, an aluminum foil conductor layer and an insulating backing layer. The drug and electrolyte reservoir layers of electrotransport delivery devices have typically been formed of hydrophilic polymers, as in, for example, Ariura et al., U.S. Pat. No. 4,474,570, Webster, U.S. Pat. No. 4,383,529, and Sasaki, U.S. Pat. No. 4,764,164. There are several reasons for using hydrophilic polymers. First, water is a biocompatible, highly polar solvent and therefore preferred for ionizing or solubilizing many drug salts. Secondly, hydrophilic polymer components (i.e., the drug reservoir in the donor electrode and the electrolyte reservoir in the counter electrode) can be hydrated while attached to the body by absorbing water from the skin or from a mucosal membrane. For example, skin contacting electrodes can be hydrated by absorbing sweat or water from transepidermal water loss. Similarly, electrodes attached to an oral mucosal membrane can be hydrated by absorbing saliva. Once the drug and electrolyte reservoirs become hydrated, ions are able to move through the reservoirs and across the tissue, enabling the device to deliver the beneficial agent to the body.

Hydrogels have been particularly favored for use as the drug reservoir matrix and electrolyte reservoir matrix in electrotransport delivery devices, in part due to their high equilibrium water content and their ability to absorb water from the body. In addition, hydrogels tend to have good biocompatibility with the skin and with mucosal membranes. However, since many drugs and certain electrode components are unstable in the presence of water, electrotransport drug delivery devices having a drug reservoir formed of a prehydrated hydrogel may also have an unacceptably short shelf life. In particular, certain therapeutic agents have limited shelf life at ambient temperature in an aqueous environment. Notable examples are insulin and prostaglandin sodium salt ($PGE_1$).

One proposed solution to the drug stability problem is to use hydrophilic polymer drug and electrolyte reservoirs which are in a substantially dry or anhydrous state, i.e. in a non-hydrated condition. The drug and/or electrolyte can be dry blended with the hydrophilic polymer and then cast or extruded to form a non-hydrated, though hydratable, drug or electrolyte containing reservoir. Alternative methods also involve the evaporation of water and/or solvent from solution or emulsion polymers to form a dry polymer film. This process is energy intensive, however, and requires a large capital investment for equipment.

In addition, the prior art non-hydrated hydrophilic polymer components must first absorb sufficient quantities of water from the body before the device can operate to deliver drug. This delay makes many devices unsuited for their intended purpose. For example, when using an iontophoretic delivery device to apply a local anesthetic in preparation for a minor surgery (e.g., surgical removal of a mole), the surgeon and the patient must wait until the drug and electrolyte reservoirs of the delivery device become sufficiently hydrated before the anesthetic is delivered in sufficient quantities to induce anesthesia. Similar delays are encountered with other drugs.

In response to these difficulties, Konno et al., in U.S. Pat. No. 4,842,577, disclose in FIG. 4 an electrotransport assembly having a substantially non-hydrated drug containing layer or membrane filter and a separate water reservoir which is initially sealed, using a foil sheet, from the drug containing portions of the electrode. Unfortunately, this electrode design is not only difficult to manufacture but also is subject to severe handling restrictions. In particular, there is a tendency for the foil seal to be inadvertently broken during manufacture, packaging and handling of the electrode. This can have particularly drastic consequences especially when the seal is broken during manufacture of the device. Once the seal is broken, water is wicked into the drug-containing reservoir which can cause degradation of the drug and/or other components before the device is ever used.

Another disadvantage of using non-hydrated hydrophilic polymer components is that they have a tendency to delaminate from other parts of the electrode assembly during hydration. For example, when utilizing a drug reservoir matrix or an electrolyte reservoir matrix composed of a hydrophilic polymer, the matrix begins to swell as it absorbs water from the skin. In the case of hydrogels, the swelling is quite pronounced. Typically, the drug or electrolyte reservoir is in either direct contact, or contact through a thin layer of an ionically conductive adhesive, with an electrode. Typically, the electrode is composed of metal (e.g., a metal foil or a thin layer of metal deposited on a backing layer) or a hydrophobic polymer containing a conductive filler (e.g., a hydrophobic polymer loaded with carbon fibers and/or metal particles). Unlike the hydrophilic drug and electrolyte reservoirs, the electrodes do not absorb water and do not swell. The different swelling properties of the hydrophilic reservoirs and the electrodes results in shearing along their contact surfaces. In severe cases, the shearing can result in the complete loss of electrical contact between the electrode and the drug/electrolyte reservoir resulting in an inoperable device.

Accordingly, there exists a need for an easily manufacturable anhydrous drug reservoir with an extended shelf life that is not susceptible to delayed hydration periods or delamination.

SUMMARY OF THE INVENTION

The present invention overcomes the long delay time and delamination problems of the prior art by providing a therapeutic agent/porous hydrophilic polymer membrane as the anhydrous drug reservoir.

More specifically, the present invention provides a multilaminate dry state electrode assembly for an electrically powered electrolytic transdermal agent delivery device. The electrode assembly has a reservoir layer including a substantially non-hydrated hydratable matrix for containing an agent to be delivered. The reservoir layer is adapted to be placed in agent-transmitting relation with a body surface and an electrode layer in electrical contact with both the reservoir layer and a power source. The reservoir layer is formed by the process of dissolving the agent in a solvent, applying the solvent and dissolved agent to a surface of a hydrophilic polymer membrane, removing the solvent from the surface of the hydrophilic polymer membrane, and disposing the agent/polymer membrane within the electrode assembly.

The present invention also provides a method of forming an anhydrous reservoir layer of an electrode assembly in an electrotransport agent delivery device. The reservoir layer is adapted to be placed in agent-transmitting relation with a body surface and an electrode in electrical contact with a power source and the reservoir layer. The method includes the steps of dissolving a beneficial agent in a solvent, applying the solvent and dissolved beneficial agent to a surface of a hydrophilic polymer membrane, removing the solvent from the surface of the polymer membrane, and disposing the beneficial agent/polymer membrane within the electrode assembly.

The solvent used in the method of the present invention may include water, ethanol, or isopropanol, for example. Further, the solvent and dissolved beneficial agent may be applied to the surface of a polyether sulfone filtration membrane or a polysulfone filtration membrane, as well as any other suitable hydrophilic polymer membrane as described herein. The solvent may be removed from the polymer membrane by drying the membrane in a forced air oven, a vacuum drying oven, a desiccator, or by lyophilizing the polymer membrane.

BRIEF DESCRIPTION OF THE DRAWINGS

The objects and advantages of the present invention will become apparent from the following detailed description of the preferred embodiments thereof in connection with the accompanying drawings in which like numerals designate like elements and in which.

DETAILED DESCRIPTION OF THE PREFERRED EMBODIMENTS

Figure 1:
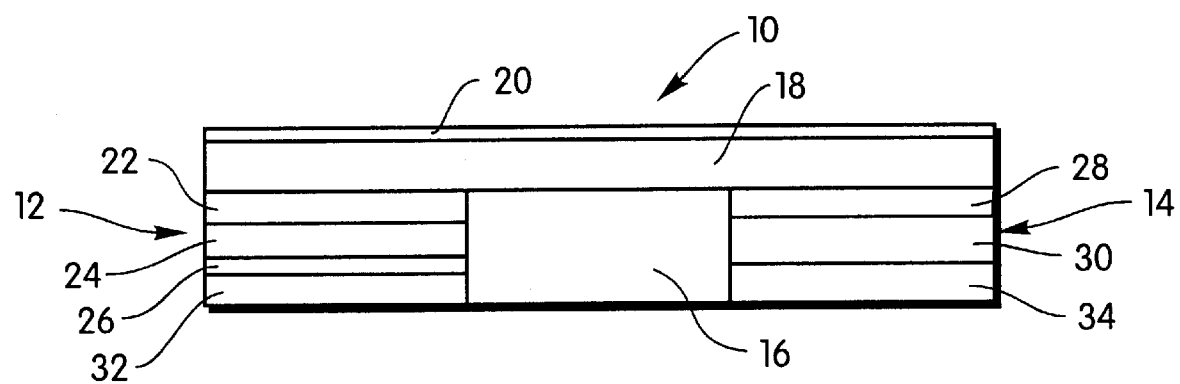
FIG. 1 is a schematic side view of an exemplary iontophoretic drug delivery device according to the present invention.

Referring to FIG. 1, an exemplary electrotransport device for delivering a beneficial or therapeutic agent through a body surface such as intact skin or a mucosal membrane is shown generally by reference numeral 10. Electrotransport delivery device 10 includes a donor electrode assembly 12 and a counter electrode assembly 14. The donor electrode assembly 12 and the counter electrode assembly 14 are physically attached to an insulator 16 and form a single self-contained unit. Insulator 16 prevents the electrode assemblies 12 and 14 from short circuiting the body by preventing electrical and/or ion transport between the electrode assemblies 12 and 14. Electrode assemblies 12 and 14 are connected in series, by appropriate electrical conductors, with an electrical power source. The power source and the electrical conductors are schematically shown as layer 18, The power source used to power device 10 is typically one or more low voltage batteries. A water impermeable backing layer 20 may preferably cover layer 18 with its associated electrical components.

The donor electrode assembly 12 typically includes an electrode layer 22 and a reservoir layer 24. The reservoir 24 contains the beneficial agent to be iontophoretically delivered by device 10 and a source of hydrating material. A rate controlling membrane layer 26 may optionally be positioned between the reservoir layer 24 and the body surface for controlling the rate at which the agent is delivered to the body surface or for preventing the delivery of agent to the body surface when the device is turned off. Counter electrode assembly 14 contacts the body surface at a location spaced apart from electrode assembly 12. Counter electrode assembly 14 include an electrode layer 28 and a reservoir layer 30. Device 10 may be adhered to the body surface by means of ion-conducting adhesive layers 32, 34. As an alternative to the ion-conducting adhesive layers 32, 34 shown in FIG. 1, device 10 may be adhered to the body surface using an adhesive overlay. Any of the conventional adhesive overlays used to secure passive transdermal delivery devices to the skin may be used in the present invention.

When used in connection with the reservoir 24 or the electrode assembly 12, the term "agent" refers to beneficial agents, such as drugs, within the class which can be delivered through body surfaces. The expression "drug" is intended to have a broad interpretation as any therapeutically active substance which is delivered to a living organism to produce a desired, usually beneficial effect. In general, this includes therapeutic agents in all of the major therapeutic areas including, but not limited to, anti-infectives such as antibiotics and antiviral agents, analgesics and analgesic combinations, anesthetics, anorexics, antiarthritics, antiasthmatic agents, anticonvulsants, antidepressants, antidiabetic agents, antidiarrheals, antihistamines, anti-inflammatory agents, antimigraine preparations, antimotion sickness preparations, antinauseants, antineoplastics, antiparkinsonism drugs, antipruritics, antipsychotics, antipyretics, antispasmodics, including gastrointestinal and urinary, anticholinergics, sympathomimetrics, xanthine derivatives, cardiovascular preparations including calcium channel blockers, beta-blockers, antiarrythmics, antihypertensives, diuretics, vasodiloators, including general, coronary, peripheral and cerebral, central nervous system stimulants, cough and cold preparations, decongestants, diagnostics, hormones, hypnotics, immunosuppressives, muscle relaxants, parasympatholytics, parasympathomimetrics, proteins, peptides, psychostimulants, sedatives and tranquilizers.

The present electrotransport delivery system is particularly useful in the controlled delivery of peptides, polypeptides, proteins, macromolecules and other drugs which have a tendency to be unstable, hydrolyzed, oxidized, denatured or otherwise degraded in the presence of the liquid, such as water, which is necessary to conduct iontophoresis. For example, drugs containing either an ester bond (i.e., steroids) or an amide bond (i.e., peptides) may be hydrolyzed in water. Specific examples of drugs which can become degraded in the presence of water include catechols, such as apomorphine and epinephrine, salbutamol, sulfhydryls such as captopril, niphedipine and peptides such as VIP and insulin. Examples of other peptides and proteins which may be delivered using the device of the present invention are set forth with particularity in U.S. Pat. No. 5,158,537 issued to Haak et al., and assigned to the present assignee, the entire contents of which are hereby incorporated by reference.

When the device 10 is in storage, no current flows because the device does not form a closed circuit. When the device is placed on the skin or mucosal membrane of a patient and the electrode assemblies 12 and 14 are sufficiently hydrated to allow ions to flow through the various layers of the electrode assemblies, the circuit between the electrodes is closed and the power source begins to deliver current through the device and through the body of the patient. The donor and counter electrode assemblies 12 and 14 normally include a strippable release liner (not shown) which is removed prior to application of the electrode assemblies to the body surface. In certain instances, it may also be desirable for the delivery of the beneficial agent through the device 10 to be controlled by the user through a user-actuated switch (not shown).

In accordance with the present invention, the donor reservoir 24 is an anhydrous reservoir containing a therapeutic agent/hydrophilic polymer membrane. The membrane is maintained in a dry state for storage, and then hydrated when ready for use. Hydration of the hydrophilic membrane may occur in any known manner, as described in further detail below.

The formation of the hydrophilic therapeutic drug/polymer membrane in accordance with the present invention includes the dissolution of the therapeutic agent in aqueous media or a water/organic solvent mixture in order to obtain a low viscosity solution. A suitable solvent would include water, ethanol, isopropanol or a combination of water and an organic solvent. The drug solution may be prepared at ambient or less than ambient temperature for thermally sensitive molecules. In addition, the drug solutions may be mixed with relatively low shear mixing equipment which substantially prevents degradation of shear sensitive molecules.

Once prepared, the solution of the therapeutic agent is applied to the surface of a selected, pre-formed, hydrophilic polymer filtration membrane. Hydrophilic within the terms of the present invention includes all polymers having a liquid absorbtion rate of generally 1–10 microliters/cm$^2$/sec or greater. A variety of polymeric hydrophilic filtration membranes suitable for use in the present invention are commercially available. Preferably, a polyether sulfone filtration membrane, such as Gelman Supor® offered by Gelman Sciences, is utilized. The Supor® 1200 having a 1.2 $\mu$ pore size is most preferred, and the manufacturer claims the polyether sulfone is low protein binding. Other membranes having an open pore size ranging from 0.5 to 10.0 $\mu$, preferably from 0.5 to 1.5 $\mu$, may also be used. Other suitable filtration membranes, also offered under tradenames by Gelman Sciences, include hydrophilic acrylic copolymer (Versapor®), hydrophilic polysulfone (HT Tuffryn®), glass fiber, hydrophilic nylon (Nylaflo®), hydrophilic mixed cellulose esters (GN Metricel®), hydrophilic polyvinylidene fluoride (FP Vericel™) and hydrophilic polypropylene (GH Polypro). The membranes having a low affinity for proteins, i.e., low protein binding membranes such as the hydrophilic polysulfone and polyether sulfone membrane filters, are particularly well suited for the present invention in order to reduce the tendency of the therapeutic agent, beneficial agent or drug to adhere to the surface of the membrane and thereby obtain a more efficient delivery thereof.

The solution may be applied to the hydrophilic polymer filtration membrane using a variety of techniques including spraying, BioDot or any other type of micrometer dispensing, dipping, volumetric metering, or other suitable coating technology. Low viscosity liquids, such as the therapeutic agent solution, are easily and reproducibly dispensed with a volumetric metering pump.

The hydrophilic polymer filtration membrane is then dried in order to remove the solvent or other aqueous media therefrom. The removal of the solvent or other aqueous media may be accomplished by drying the filtration membrane in a forced air oven, vacuum drying oven, desiccator, or by lyophilization. The drying operation is performed for a period of time sufficient to obtain an approximately 10% or less residual moisture content in the membrane, more preferably an approximately 5% or less residual moisture content, and most preferably, a 1% or less residual moisture content. The finished anhydrous membranes generally contain from 0.1 to 5.0 mg/cm$^2$ of therapeutic agent/membrane. The overall size of the anhydrous membrane will of course vary dependent upon the therapeutic agent and the amount thereof contained therein, but generally, anhydrous membranes on the order of 1 to 12 cm$^2$ will be cut for placement into the appropriate reservoirs of the electrotransport system.

Thus, the preparation of the therapeutic agent/hydrophilic filtration membrane affords a dry polymer matrix which enhances the storage stability of drug molecules that do not possess long term stability in an aqueous environment. In the anhydrous state, the polymer matrix has an extended shelf life and is not subject to the disadvantages and problems encountered with the storage of water sensitive therapeutic agents. The anhydrous or dry therapeutic agent/polymer membrane may be kept in dry storage until ready for use and then hydrated with a suitable hydrogel matrix, such as, preferably, a poly(vinyl alcohol) based hydrogel having a water content of approximately 75.0% to 95.0%. Other suitable hydrogels would include an adhesive hydrogel or a hydrated hydroxy propyl cellulose hydrogel, for example. Other sources of a hydrating material could of course also be used in the present invention, such as, for example, a liquid pouch as described in U.S. Pat. No. 5,158,537 or a liquid passageway as described in U.S. Pat. No. 5,385,543, the contents of both of which are hereby incorporated by reference.

Figure 2A:
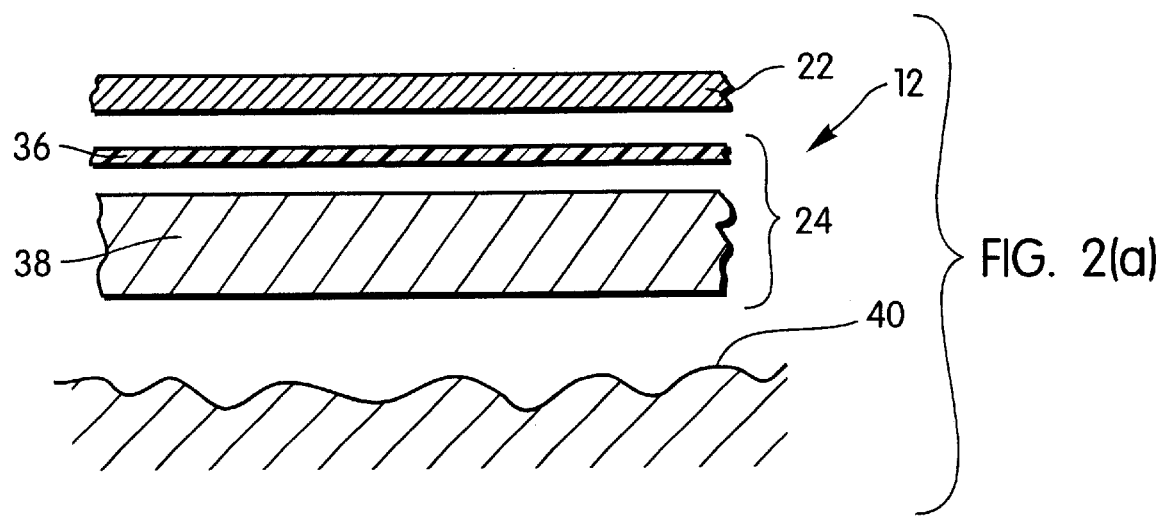
FIG. 2(a) is an exploded schematic view of an anhydrous reservoir layer of the device of FIG. 1.
Figure 2B:
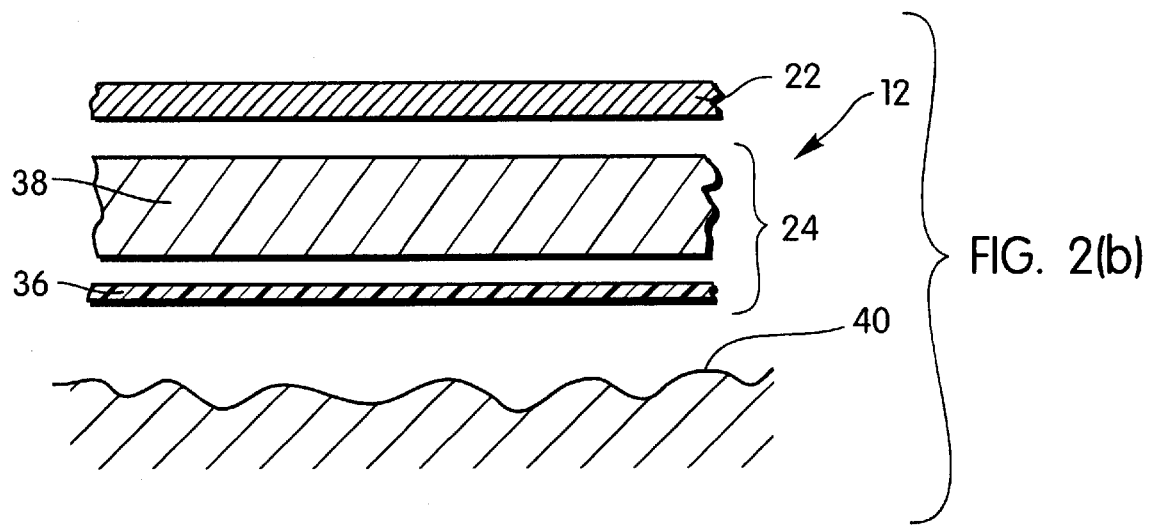
FIG. 2(b) is an exploded schematic view of a further embodiment of an anhydrous reservoir layer of the device of FIG. 1.
Figure 2C:
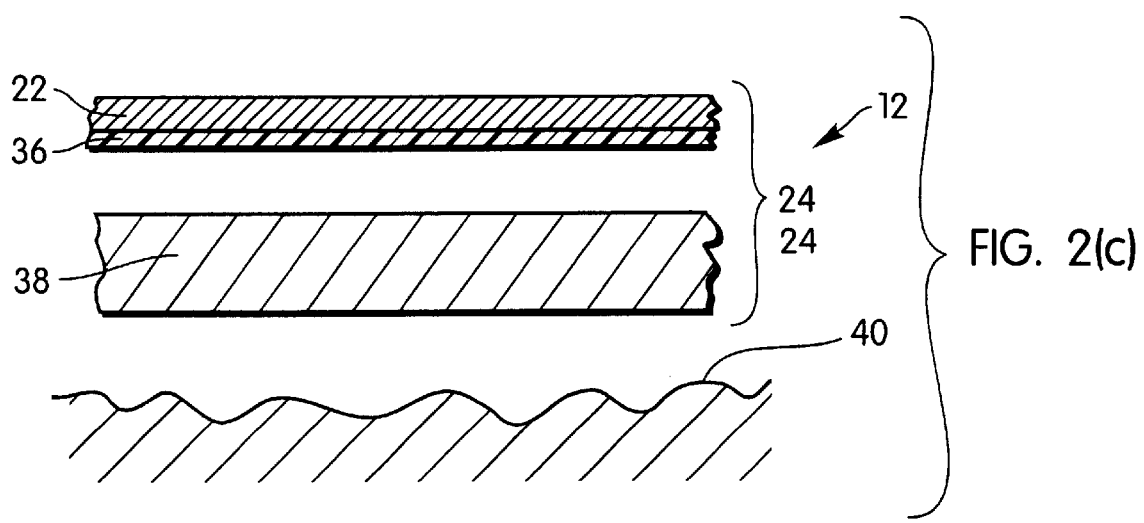
FIG. 2(c) is an exploded schematic view of yet another embodiment of an anhydrous reservoir layer of the device of FIG. 1.

Possible configurations of the electrotransport system of the present invention are shown in the exploded schematics of FIGS. 2(a)–2(c), wherein reservoir 24 includes the therapeutic agenthydrophilic polymer membrane 36 and a suitable source of hydrating material 38. In FIG. 2(a), the hydrating material 38 comprises a hydrogel disposed proximate to the skin surface 40, the therapeutic agent/polymer membrane 36 is disposed thereabove, and an Ag foil anode comprising the electrode layer 22 is thereabove forming the outermost layer of the electrode assembly 12. Alternatively, as shown in FIG. 2(b), the therapeutic agent/polymer membrane 36 is proximate to the skin 40, the source of hydrating material 38 is disposed thereabove, and the Ag foil anode comprising the electrode layer 22 is thereabove, again forming the outermost layer of the electrode assembly 12. Still further, as illustrated in FIG. 2(c), the source of hydrating material 38 is disposed proximate to the skin surface 40, the therapeutic agent/polymer membrane 36 is disposed thereabove, and Ag/AgCl ink is screen printed onto the membrane 36 to form the electrode layer 22 and thereby afford a system that includes an universal electrode and a drug matrix.

The therapeutic agenthydrophilic filtration membrane of the present invention is very thin, generally on the order of two to ten mils, more preferably 3 to 6 mils. The rate of hydration obtained in the present invention is therefore extremely rapid, with hydration being obtained generally within ten seconds after placement of the membrane in contact with a hydrogel or other hydrating source. Thus, the electrotransport of the therapeutic agent is not delayed as in the prior art devices. The hydrated membrane also remains firmly adhered to the hydrogel, which is partially due to the dimensional stability of the hydrated membrane.

EXAMPLE 1

Experimental studies were conducted to compare drug delivery from a donor comprised of an imbibed membrane/blank gel to a control hydrogel, with alniditan being used as the model compound. 2 cm² disks of a filtration membrane were punched using a stainless steel punch. The disks were imbibed with about 14.2 $\mu$l of drug solution (at pH 8.0) and dried at ambient. The alniditan imbibed membranes each contained about 4 mg alniditan/membrane.

Flux of alniditan through human epidermis was then tested according to the following configurations:

I. Alniditan imbibed membranes were placed between a blank gel comprising 15% polyvinyl alcohol (2 cm²×0.16 cm) and human epidermis.

II. Alniditan imbibed membranes were placed between a blank gel comprising 15% polyvinyl alcohol (2 cm²×0.16 cm) and a silver foil anode and the blank gel was in contact with human epidermis.

III. A control gel comprising 15% polyvinyl alcohol, 2% hydroxypropyl methyl cellulose, and 2.5% alniditan (pH 8.09, 2 cm²×0.16 cm) was formulated and comprised about 8 mg drug/gel which was placed directly on human epidermis.

The above alniditan formulations were placed in the donor compartment of a large Delrin receptor and donor gel configuration. A silver foil was used as the donor electrode and an extruded laminate comprising a silver chloride/polyisobutylene formulation was used as the receptor electrode. The receptor solution was 3% Dulbeccos Phosphate Buffer Solution. A total of 0.6 mA of electric current was applied at a current density of 0.3 mA/cm².

Figure 3:
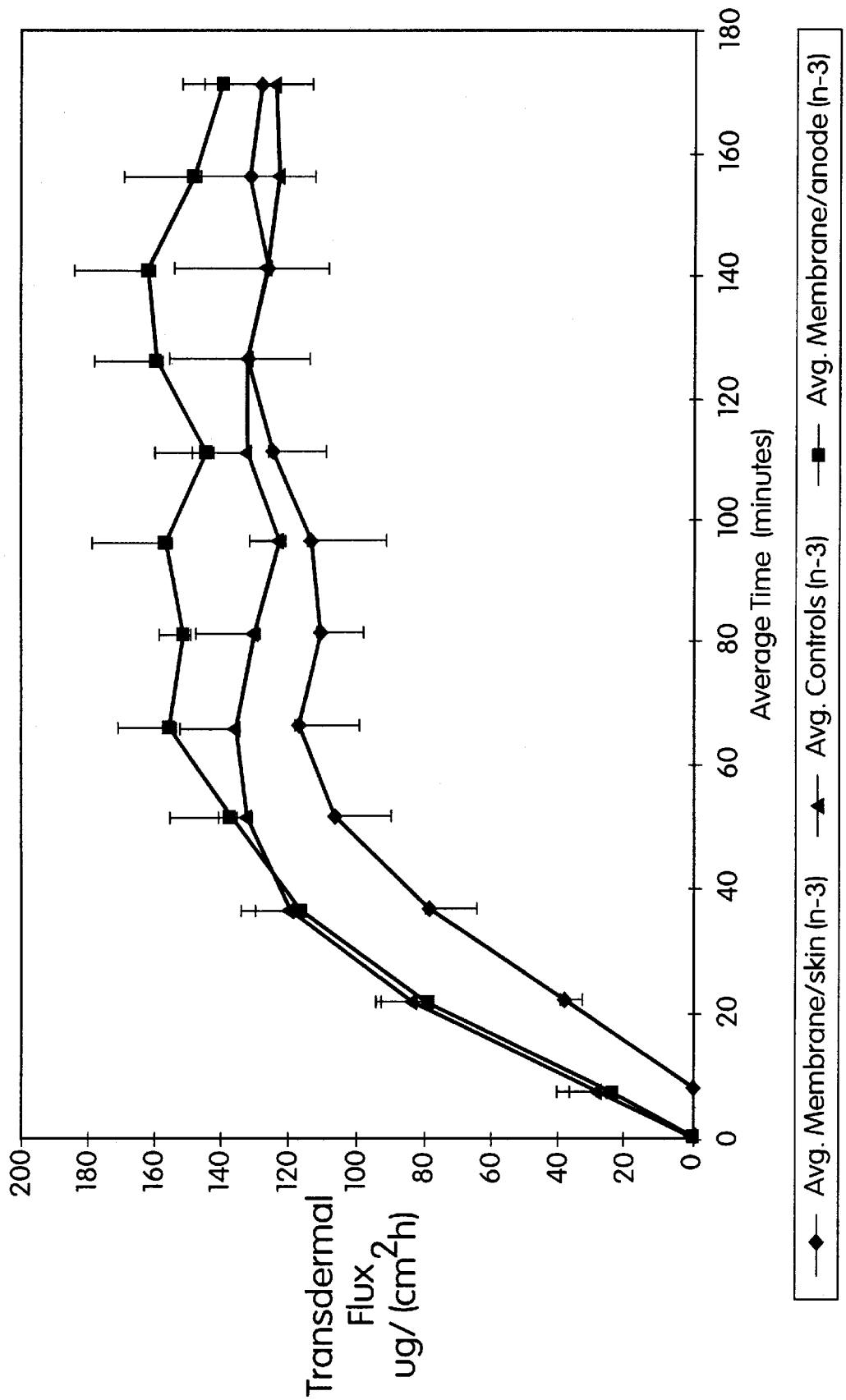
FIG. 3 is a graphical representation of the transdermal flux obtained in an experimental analysis of the device of the present invention.

As shown in the graph presented in FIG. 3, the transdermal flux obtained with the filtration membrane of the present invention was sufficient to overcome the long delay times of prior art dry state reservoirs.

Having thus generally described our invention and described in detail certain preferred embodiments thereof, it will be readily apparent that various modifications to the invention may be made by workers skilled in the art without departing from the scope of this invention and which is limited only by the following claims.

Wherein, what is claimed is:

1. A multilaminate dry state electrode assembly for an electrically powered electrotransport agent delivery device, the electrode assembly having a reservoir layer and an electrode layer the reservoir layer being adapted to be placed in agent-transmitting relation with a body surface, the reservoir layer comprising a substantially non-hydrated hydratable matrix for containing an agent to be delivered, said matrix having a body surface distal side and a body surface proximal side, said reservoir further comprising a hydrating material layer, said hydrating material layer located either between the electrode layer and the matrix or on the body surface proximal side of the matrix, and the electrode layer being in electrical contact with the reservoir layer and adapted to be placed in electrical contact with a power source, the reservour layer formed by the process of:

dissolving the agent in a solvent;

applying the solvent and dissolved agent to a surface of a hydrophilic polymer fitration membrane;

removing the solvent from the surface of the hydrophilic polymer filtration membrane;

disposing the agent/polymer filtration membrane within the electrode assembly.

2. The electrode assembly of claim 1 wherein the solvent comprises water.

3. The electrode assembly of claim 1 wherein the solvent comprises ethanol.

4. The electrode assembly of claim 1 wherein the solvent comprises isopropanol.

5. The electrode assembly of claim 1 wherein said hydrophilic polymer filtration membrane comprises a polyether sulfone filtration membrane.

6. The electrode assembly of claim 1 wherein said hydrophilic polymer membrane comprises a polysulfone filtration membrane.

7. A multilaminate dry state electrode assembly for an electrotransport agent delivery device, said electrode assembly comprising:

an electrode layer a reservour layer including a substantially non-hydrated hydratable matrix adapted to contain an agent to be delivered, the reservoir layer being adapted to be placed in agent-transmitting relation with a body surface, said matrix having a body surface distal side and a body surface proximal side, said reservoir further comprising a hydrating material layer, said hydrating material layer located either between the electrode and the matrix or on the body surface proximal side of the matrix, the an electrode layer in electrical contact with the reservoir layer and adapated to be placed in electrical contact with a power source, wherein said hydratable matrix comprises a hydrophilic polymer filtration membrane.

8. The electrode assembly of claim 7 wherein said filtration membrane is microporous.

9. The electrode assembly of claim 8 wherein said filtration membrane has a pore size between 0.5 and 10.0$\mu$.

10. The electrode assembly of claim 9 wherein said filtration membrane has a pore size between 0.5 and 1.5$\mu$.

11. The electrode assembly of claim 7 wherein the filtration membrane is selected from the group consisting of acrylic copolymers, glass fiber, nylon, mixed cellulose esters, polyvinylidene fluoride, and polypropylene.

12. The electrode assembly of claim 7 wherein said filtration membrane comprises a polyether sulfone filtration membrane.

13. The electrode assembly of claim 7 wherein said filtration membrane comprises a polysulfone filtration membrane.

14. The electrode assembly of claim 7 wherein the filtration membrane comprises a thickness of about 2–10 mils.

15. The electrode assembly of claim 14 wherein the thickness is about 3–6 mils.

16. The electrode assembly of claim 7 wherein the matrix is imbibed with drug before incorporation into the electrotransport device.

* * * * *